United States Patent [19]

Kinsho et al.

[11] Patent Number: 5,514,824
[45] Date of Patent: May 7, 1996

[54] PROCESS FOR PREPARING SILACYCLOHEXANE-BASE LIQUID CRYSTAL COMPOUNDS

[75] Inventors: Takeshi Kinsho; Takaaki Shimizu; Tsutomu Ogihara; Tatsushi Kaneko; Mutsuo Nakashima, all of Niigata, Japan

[73] Assignee: Shin-Etsu Chemical Co., Ltd., Tokyo, Japan

[21] Appl. No.: 501,522

[22] Filed: Jul. 12, 1995

[30] Foreign Application Priority Data

Jul. 12, 1994 [JP] Japan ................. 6-182903

[51] Int. Cl.$^6$ ................. C07F 7/08; C07F 7/18
[52] U.S. Cl. .............. 556/406; 204/157.44; 204/157.45; 204/157.64; 204/157.74
[58] Field of Search ............. 556/406; 204/157.44, 204/157.45, 157.64, 157.74

[56] References Cited

U.S. PATENT DOCUMENTS 4,973,723 11/1990 Cawthorn et al. ............. 556/406
5,454,977 10/1995 Shimizu et al. ............. 556/406 X

FOREIGN PATENT DOCUMENTS 0632044 1/1995 European Pat. Off. .

*Primary Examiner*—Paul F. Shaver
*Attorney, Agent, or Firm*—Lowe, Price, LeBlanc & Becker

[57] ABSTRACT

A process for preparing silacyclohexane-based liquid crystal compounds of the formula which comprises reacting ketone compounds of the following general formula Ar represents a phenyl or tolyl group, and R represents Ar, a substituted or unsubstituted alkyl group, with an organometal reagent such as a Grignard reagent or an organotitanium, organolithium or organozinc compound, followed by dehydration, oxidation, de-silylation and reduction to obtain silacyclohexane-based liquid crystal compounds of the type mentioned below.

wherein Y is halogen and i is a value of 0, 1, 2 or 3, and A represents a substituted phenyl group or tolyl group or a halogen or functional group such as CN, Cl, Br, $OCF_3$, $OCHF_2$ etc.

21 Claims, No Drawings

PROCESS FOR PREPARING SILACYCLOHEXANE-BASE LIQUID CRYSTAL COMPOUNDS

BACKGROUND OF THE INVENTION

1. Field of The Invention

This invention relates to the preparation of silacyclohexane-based liquid crystal compounds.

2. Description of the Related Art

The liquid crystal display devices make use of optical anisotropy and dielectric anisotropy of liquid crystal substances. Depending on the mode of display, there are a variety of display systems including those of a twisted nematic type (TN type), a supertwisted nematic type (STN type), a super birefringence type (SBE type), a dynamic scattering type (DS type), a guest/host type, a type of deformation of aligned phase (DAP type), a polymer dispersion type (PD type), and an optical mode interference type (OMI type). The most popular display device is one which is based on the SchadtHelfrich effect and has a twisted nematic structure.

Although the properties of the liquid crystal substances used in these liquid crystal devices depend, more or less, on the type of display, it is commonly required that the liquid crystal substances have a wide range of liquid crystal working temperatures and that they be stable against moisture, air, light, heat, electric field and the like. Moreover, the liquid crystal substances should desirably be low in viscosity and should ensure a short address time, a low threshold voltage and a high contrast in a cell.

As the liquid crystal display devices have wider utility in recent years, the characteristic properties required for liquid crystal materials become much severer. In addition, those characteristics which have never been required for conventional liquid crystal substances are now expected such as a lower drive voltage, a wider working temperature range which can satisfy the on-vehicle needs and an improvement in low temperature performance.

Under these circumstances, we developed novel liquid crystal compounds which contain a silicon atom in the molecule so that the characteristic properties for use as a liquid crystal substance are improved, In fact, we proposed the liquid crystal compounds in co-pending U.S. application Ser. Nos. 08/36964 and 08/23195 (corresponding to European Patent Application Nos. 94/20414.1 and 94/17287.2 and Korean Patent Application Nos. 94-35603 and 94-28226, respectively).

SUMMARY OF THE INVENTION

It is an object of the invention to provide a novel process for preparing silacyclohexane-based liquid crystal compounds.

The above object can be achieved, according to one embodiment of the invention, by a process for preparing a silacyclohexane-based liquid crystal compound of the following general formula (I)

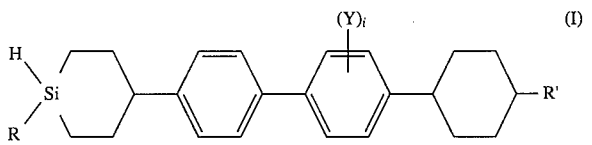

wherein R is a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms or an alkoxyalkyl group having from 2 to 7 carbon atoms, Y represents a halogen, preferably F or Cl or $CH_3$, and i is a value of 0, 1, 2 or 3, and R' represents a linear alkyl group having from 1 to 10 carbon atoms, a mono or difluoroalkyl group having from 1 to 10 carbon atoms, a branched alkyl group having from 3 to 8 carbon atoms or an alkoxyalkyl group having from 2 to 7 carbon atoms, the process comprising the steps of:

subjecting a ketone compound of the following general formula (1)

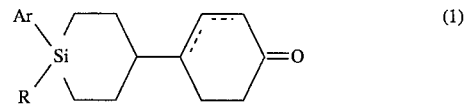

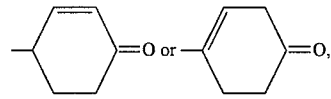

Ar represents a phenyl group or a tolyl group, R has the same meaning as defined above, to reaction with an organometal reagent of the following general formula (2)

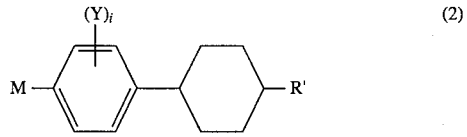

wherein M represents Li, MgU, ZnU or $TiU_k(OW)_{3-k}$ in which U represents a halogen, preferably Cl, Br or I, W represents an alkyl group preferably having from 1 to 6 carbon atoms, and k is zero or an integer of 1 to 3, Y, i and R' have, respectively, the same meanings as defined in the formula (I) to obtain a compound of the following general formula (3)

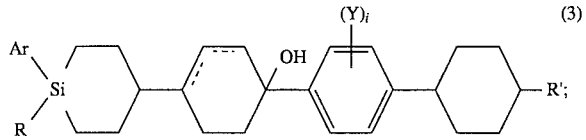

subjecting the compound of the general formula (3) to dehydration and then to oxidation, i.e. dehydrogenation, to obtain a compound of the following general formula (4)

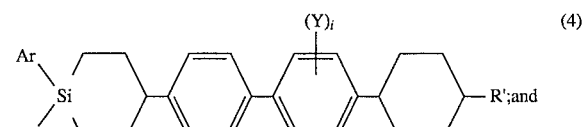

subjecting the compound of the general formula (4) to de-silylation and then to reduction to obtain the silacyclohexane-based compound of the general formula (I) defined hereinabove.

According to another embodiment of the invention, there is also provided a process for preparing another type of silacyclohexane-based liquid crystal compound of the following general formula (II)

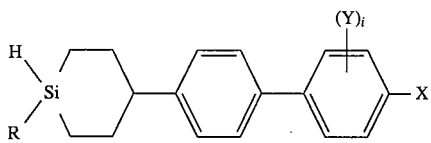

wherein R, Y and i have., respectively, the same meanings as defined in the formula (I), i.e. R represents a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms or an alkoxyalkyl group having from 2 to 7 carbon atoms, Y represents a halogen, preferably F or Cl, or $CH_3$, and i is a value of 0, 1, 2 or 3, and X represents g or OR wherein R has the same meaning as defined above, CN, F, Cl, Br, $CF_3$, $OCF_3$, $OCHF_2$, $OCHFCl$, $OCF_2Cl$, $CF_2Cl$, $—(O)_m—C\ Y_1=CX_1X_2$ wherein m is a value of 0 or 1, $Y_1$ and $X_1$, respectively, represent H, F or Cl, and $X_2$ represents F or Cl, or $—O—(CH_2)_r(CF_2)_sX_3$ wherein r and s are, respectively, a value of 0, 1 or 2 provided that r+s=2, 3 or 4, and $X_3$ represents H, F or C, the process comprising the steps of:

subjecting a ketone compound of the following general formula (1)

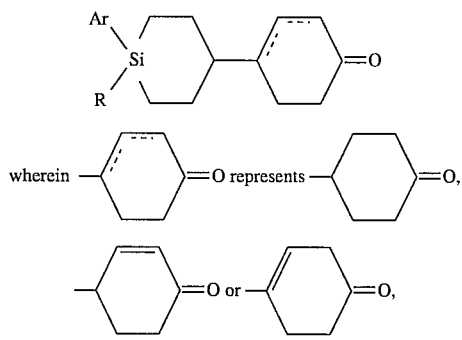

Ar represents a phenyl group or a tolyl group, R has the same meaning as defined above, to reaction with an organometal reagent of the following general formula (5)

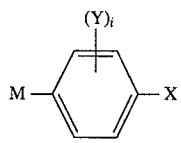

wherein M represents Li, MgU, ZnU or $TiU_k(OW)_{3-k}$ in which U represents a halogen, preferably Cl, Br or I, W represents an alkyl group preferably having from 1 to 6 carbon atoms, and k is zero or an integer of 1 to 3, Y, i and X have, respectively, the same meanings as defined above to obtain a compound of the following general formula (6)

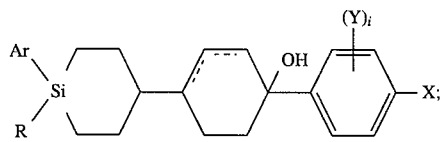

subjecting the compound of the general formula (6) to dehydration and then to oxidation, i.e. dehydrogenation, to obtain a compound of the following general formula (7)

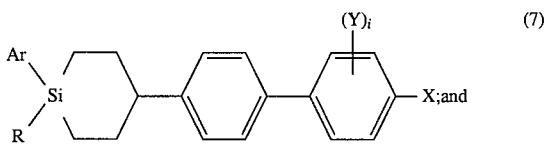

subjecting the compound of the general formula (7) to de-silylation and then to reduction to obtain the silacyclohexane-based compound of the general formula (II) defined hereinabove.

According to a further embodiment of the invention, there is provided a process for preparing other type of silacyclohexane-based liquid crystal compound of the following general formula (III)

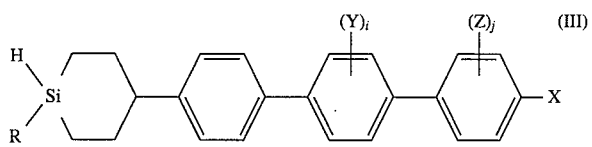

wherein R, Y and i have, respectively, the same meanings as defined in the foregoing formulas, i.e. R represents a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms or an alkoxyalkyl group having from 2 to 7 carbon atoms, Y represents a halogen, preferably F or Cl, or $CH_3$, and i is a value of 0, 1, 2 or 3, and X represents R or OR, in which R has the same meaning as defined above, CN, F, Cl, Br, $CF_3$, $OCF_3$, $OCHF_2$, $OCHFCl$, $OCF_2Cl$, $CF_2Cl$, $—(O)_m—C\ Y_1=CX_1X_2$ wherein m is a value of 0 or 1, $Y_1$ and $X_1$, respectively, represent H, F or Cl, and $X_2$ represents F or Cl, or $—O—(CH_2)_r(CF_2)_sX_3$ wherein r and s are, respectively, a value of 0, 1 or 2 provided that r+s=2, 3 or 4, and $X_3$ represents H, F or Cl, Z represents a halogen, preferably F or Cl, or $CH_3$ and i is a value of 0, 1, 2 or 3, the process comprising the steps of:

subjecting a ketone compound of the following general formula (1)

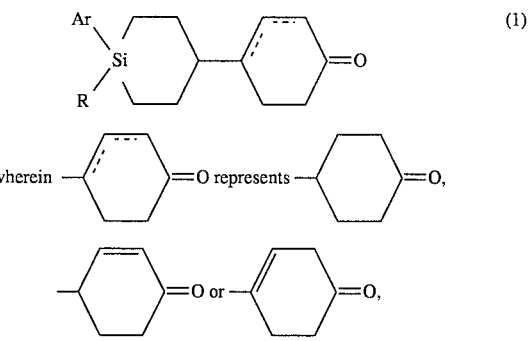

Ar represents a phenyl group or a tolyl group, R has the same meaning as defined above, to reaction with an organometal reagent of the following general formula (8)

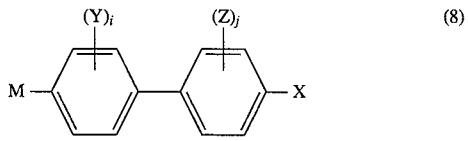

wherein M represents Li, MgU, ZnU or $TiU_k(OW)_{3-k}$ in which U represents a halogen, preferably Cl, Br or I, W represents an alkyl group preferably having from 1 to 6 carbon atoms, and k is zero or an integer of 1 to 3, Y, Z, i, j and X have, respectively, the same meanings as defined above to obtain a compound of the following general formula (9)

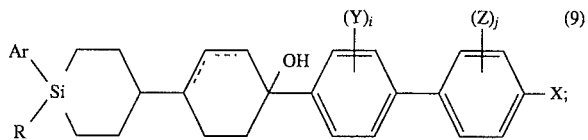

subjecting the compound of the general formula (9) to dehydration and then to oxidation, i.e. dehydrogenation, to obtain a compound of the following general formula (10)

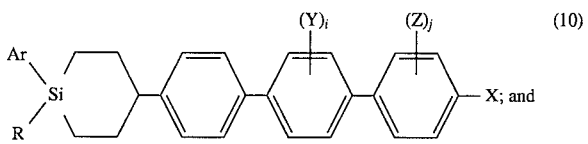

subjecting the compound of the general formula (10) to de-silylation and then to reduction to obtain the silacyclohexane-based compound of the general formula (III) defined hereinabove.

DETAILED DESCRIPTION OF THE INVENTION

The embodiments of the invention are described. It will be noted that Ar, R, R', X, Y, Z, i, and j which have, respectively, been defined in the foregoing formulas may not be sometimes defined again in the formulas appearing hereinafter.

One of the starting materials used in the processes for preparing silacyclohexane liquid crystal compounds according to the embodiments of the invention is a ketone compound of the following general formula (1)

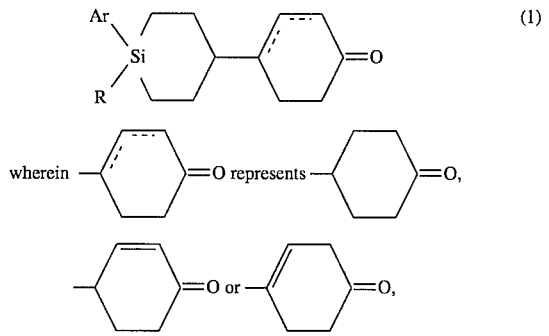

Ar represents a phenyl group or a tolyl group, and R is a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms or an alkoxyalkyl group having from 2 to 7 carbon atoms. The preparation of this ketone compound is set out in our earlier Japanese Patent Application No. 6-154219, filed Jun. 13, 1994 (corresponding to co-pending U.S. patent application, filed Jun. 7, 1995 and not yet numbered on record).

Examples of the linear alkyl group having from 1 to 10 carbon represented by R include methyl, ethyl, n-propyl, n-butyl, n-pentyl, n-hexyl, n-heptyl, n-octyl, n-nonyl and n-decyl. Examples of the mono or difluoroalkyl group having from 1 to 10 carbon atoms include fluoromethyl, 1-fluoroethyl, 1-fluoropropyl, 1-fluorobutyl, 1-fluoropentyl, 1-fluorohexyl, 1-fluorooctyl, 1-fluorononyl, 1-fluorodecyl, 2-fluoroethyl, 2-fluoropropyl, 2-fluorobutyl, 2-fluoropentyl, 2-fluorohexyl, 2-fluoroheptyl, 2-fluorooctyl, 2-fluorononyl, 2-fluorodecyl, 3-fluoropropyl, 3-fluorobutyl, 3-fluoropentyl, 3-fluorohexyl, 3-fluoroheptyl, 3-fluorooctyl, 3-fluorononyl, 3-fluorodecyl, 4-fluorobutyl, 4-fluoropentyl, 4-fluorohexyl, 4-fluoroheptyl, 4-fluorooctyl, 4-fluorononyl, 4-fluorodecyl, 5-fluoropentyl, 5-fluorohexyl, 5-fluoroheptyl, 5-fluorooctyl, 5-fluorononyl, 5-fluorodecyl, 6-fluorohexyl, 6-fluoroheptyl, 6-fluorononyl, 6-fluorodecyl, 7-fluoroheptyl, 7-fluorooctyl, 7-fluorononyl, 7-fluorodecyl, 8-fluorooctyl, 8-fluorononyl, 8-fluorodecyl, 9-fluorononyl, 9-fluorodecyl, 10-fluorodecyl, difluoromethyl, 1,1-difluoroethyl, 1,1-difluoropropyl, 1,1-difluorobutyl, 1,1-difluoropentyl, 1,1-difluorohexyl, 1,1-difluoroheptyl, 1,1-difluorooctyl, 1,1-difluorononyl, 1,1-difluorodecyl, 2,2difluoroethyl, 2,2-difluoropropyl, 2,2-difluorobutyl, 2,2-difluoropentyl, 2,2-difluorohexyl, 2,2-difluoroheptyl, 2,2-difluorooctyl, 2,2-difluorononyl, 2,2-difluorodecyl, 3,3-difluoropropyl, 3,3-difluorobutyl, 3,3-difluoropentyl, 3,3-difluorohexyl, 3,3-difluoroheptyl, 3,3-difluorooctyl, 3,3-difluorononyl, 3,3-difluorodecyl, 4,4-difluorobutyl, 4,4-difluoropentyl, 4,4-difluorohexyl, 4,4-difluoroheptyl, 4,4-difluorooctyl, 4,4-difluorononyl, 4,4-difluorodecyl, 5,5-difluoropentyl, 5,5-difluorohexyl, 5,5-difluoroheptyl, 5,5-difluorooctyl, 5,5-difluorononyl, 5,5-difluorodecyl, 6,6-difluorohexyl, 6,6-difluoroheptyl, 6,6-difluorooctyl, 6,6-difluorononyl, 6,6-difluorodecyl, 7,7-difluoroheptyl, 7,7-difluorooctyl, 7,7-difluorononyl, 7,7-difluorodecyl, 8,8-difluorooctyl, 8,8-difluorononyl, 8,8-difluorodecyl, 9,9-difluorononyl, 9,9-difluorodecyl and 10,10-difluorodecyl.

Examples of the branched alkyl group having 3 to 8 carbon atoms include isopropyl, 1-methylpropyl, 2-methylpropyl, sec-butyl, iso-butyl, 1-methylbutyl, 2-methylbutyl, 3-methylbutyl, 1-methylpentyl, 2-methylpentyl, 3-methylpentyl, 1-ethylpentyl, 1-methylhexyl, 2-methylhexyl, 3-methylhexyl, 2-ethylhexyl, 3-ethylhexyl, 1-methylheptyl, 2-methylheptyl and 3-methylheptyl.

Examples of the alkoxyalkyl group having from 2 to 7 carbon atoms include methoxymethyl, ethoxymethyl, propoxymethyl, butoxymethyl, pentoxymethyl, hexyloxymethyl, methoxyethyl, ethoxyethyl, propoxyethyl, butoxyethyl, methoxypropyl, ethoxypropyl, propoxypropyl, butoxypropyl, methoxybutyl, ethoxybutyl, propoxybutyl, methoxypentyl and ethoxypentyl.

Of these, preferred linear alkyl groups are ones having from 3 to 7 carbon atoms and include, for example, n-propyl, n-butyl, n-pentyl, n-hexyl and n-heptyl. Likewise, preferred mono or difluoroalkyl groups include 2-fluoroethyl, 2-fluoropropyl, 2-fluorobutyl, 2-fluoropentyl, 2-fluorohexyl, 2-fluoroheptyl, 4-fluorobutyl, 4-fluoropentyl, 4-fluorohexyl, 4-fluoroheptyl, 5-fluoroheptyl, 6-fluorohexyl, 7-fluoroheptyl, 2,2-difluoroethyl, 2,2-difluoropropyl, 2,2-difluorobutyl, 2,2-difluoropentyl, 2,2-difluorohexyl, 2,2-difluoroheptyl, 4,4-difluorobutyl, 4,4-difluoropentyl, 4,4-difluorohexyl, 4,4-difluoroheptyl, 5,5-difluoropentyl, 5,5-difluorohexyl, 5,5--difluoroheptyl, 6,6-difluorohexyl, 6,6-difluoroheptyl and 7,7-difluoroheptyl.

Preferred branched alkyl groups include, for example, isopropyl, 1-methylpentyl, 2-methylpentyl, 1-methylbutyl, 2-methylbutyl, 3-methylbutyl, 1-methylpentyl and 2-ethylhexyl.

Preferred alkoxyalkyl groups include methoxymethyl, methoxyethyl, methoxypropyl, methoxypentyl, ethoxymethyl, ethoxyethyl, propoxymethyl and pentoxymethyl.

According to the invention, the ketone compound of the formula (1) is reacted with an organometal reagent represented by the following general (11)

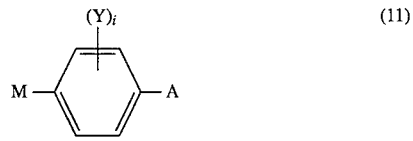

wherein M represents Li, MgU, ZnU or $TiU_k(OW)_{3-k}$ in which U represents a halogen, preferably Cl, Br or I, W represents an alkyl group preferably having from 1 to 6 carbon atoms, and k is zero or an integer of 1 to 3, Y represents a halogen, preferably F or Cl, or $CH_3$, and i is a value of 0, 1, 2 or 3, and A represents a group of the formula (a), (b) or (c): (a) a group of the following formula (12)

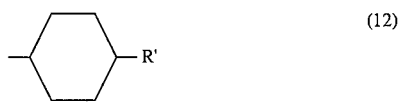

in which R' represents a linear alkyl group having from 1 to 10 carbon atoms, a mono or difluoroalkyl group having from 1 to 10 carbon atoms, a branched alkyl group having from 3 to 8 carbon atoms or an alkoxyalkyl group having from 2 to 7 carbon atoms; (b) a group of -X representing R or OR, wherein R has the same meaning as defined above with respect to the general formula (1), CN, F, Cl, Br, $CF_3$, $OCF_3$, $OCHF_2$, $OCHFCl$, $OCF_2Cl$, $CF_2Cl$, $—(O)_m—CY_1=CX_1X_2$ wherein m is a value of 0 or 1, $Y_1$ and $X_1$, respectively, represent H, F or Cl, and $X_2$ represents F or Cl, or $—O—CH_2)_r(CF_2)_sX_3$ wherein r and s are, respectively, a value of 0, 1 or 2 provided that r+s=2, 3 or 4, and $X_3$ represents H, F or Cl; or (c) a group represented by the following general formula (13)

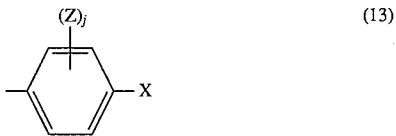

wherein Z represents a halogen, preferably F or Cl, or $CH_3$ and i is a value of 0, 1, 2 or 3, and X has the same meaning as defined just above, thereby obtaining an alcohol compound of the following general formula (14)

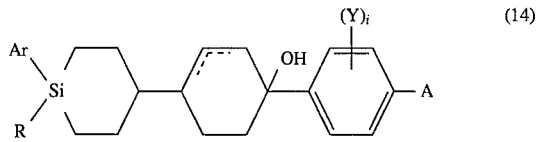

It should be noted that specific examples of the linear alkyl group having from 1 to 10 carbon atoms, mono or difluoroalkyl group having from 1 to 10 carbon atoms, branched alkyl group having from 3 to 8 carbon atoms or alkoxyalkyl group having from 2 to 7 carbon atoms represented by R' are those set out with respect to R.

The organometal reagents represented by the general formula (11) include, for example, Gringnard reagents, organozinc reagents, organotitanium reagents and organolithium reagents. Although not limitative, specific examples are set forth in examples appearing hereinafter. The reaction with any of these reagents proceds in high yield. The reaction is usually effected in a solvent. Examples of the solvent include ethers such as tetrahydrofuran, diethyl ether, di-n-butyl ether, 1,4dioxane and the like, used alone or in combination with hydrocarbons such as benzene, toluene, xylene, cumene, n-hexane, n-heptane, iso-octane and the like, or polar solvents such as N,N-dimethylformamide, dimethylsulfoxide, hexanemethylphosphoric triamide, 1,3-dimethyl-2imidazolidinone, N,N'-dimethylpropyleneurea and the like.

The reaction conditions are not critical and may depend on the type of ketone and the structure of the organometal used and preferably include a temperature of from −70° to 150° C. and a time of from 30 minutes to 5 hours. More preferably, the reaction temperature is in the range of −70° C. to 0° C. for the organolithium reagents and in the range of from room temperature to 150° C. for Mg, Ti and Zn-containing reagents.

Thereafter, the alcohol compound is subjected to dehydration reaction in the presence of an acidic catalyst to obtain a monoene or diene compound. This is particularly shown in the following reaction formula (15)

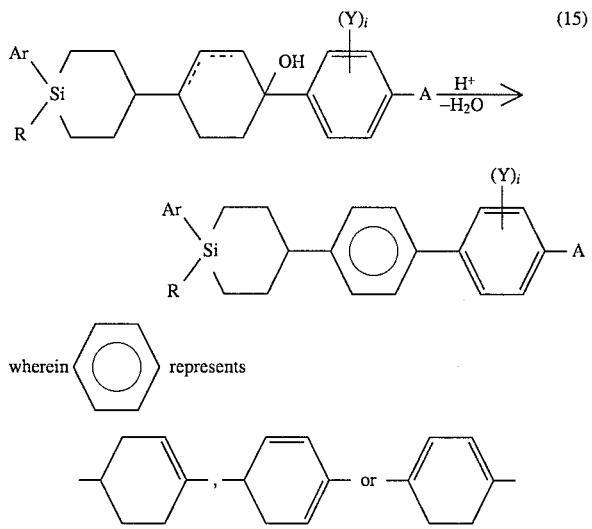

The acidic substances used for the dehydration reaction include inorganic acids such as hydrochloric acid, sulfuric acid, nitric acid and the like and salts thereof, and organic acids such as p-toluenesulfonic acid, camphorsulfonic acid, trifluoroacetic acid and the like. In order to quickly remove water generated during the reaction, it is preferred to use, as a solvent, hydrocarbons such as benzene, toluene, xylene, cumene, hexane, iso-octane and the like. By this, the reaction is azeotropically speeded up.

Subsequently, the reaction product is subjected to oxidation or dehydrogenation by which aromatization takes place as shown in the following formula (16)

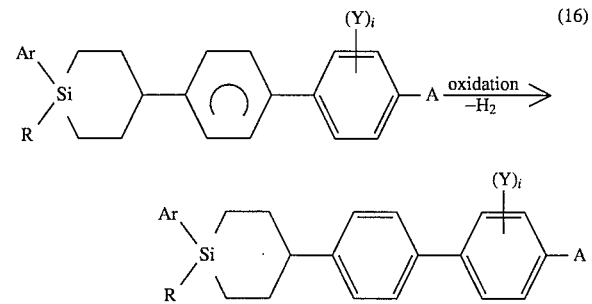

This oxidation reaction is conducted according to the following procedures: (1) a catalytic dehydrogenation reaction wherein metal catalysts employed for ordinary catalytic reduction are used; (2) a dehydrogenation reaction using quinones; and (3) a procedure including two steps of halogenation with halogenating agents and dehydrohalogenation.

1) The catalytic dehydrogenation reaction proceeds in the presence of a metal catalyst under heating conditions in a temperature range of 50° to 200° C. The metal catalysts useful for the reaction include palladium, platinum, rhodium, nickel, ruthenium and the like although oxides thereof may be used. In practice, good results are obtained when using palladium-carbon, platinum-barium sulfate, palladium-diatomaceous earth, platinum oxide, platinum-carbon, rhodium-carbon, Raney nickel, palladium oxide, nickel-diatomaceous earth, and other palladium and Ni catalysts. In order to absorb generated hydrogen, the reaction system may coexist with gases such as oxygen, air and the like, or with alkynes such as hexyne, octyne, decyne and the like or alkenes such as hexene, decene, cyclohexene and the like.

2) The quinones used for the dehydrogenation reaction include 2,3-dichloro-5,6-dicyano-1,4-benzoquinone, p-chloranil, o-chloranil, 9,10-phenanthraquinone or nitro derivatives thereof, diphenoquinones such as 3,3',5,5'tetrachloro-4,4'-diphenoquinone, and the like. The reaction is usually effected by heating the monoene or diene and a quinone in an inert solvent, such as benzene, toluene, xylene, chlorobenzene, hexane, iso-octane, dioxane or the like under reflux.

3) Preferred examples of the halogenating agents used in the halogenation-dehydrohalogenation reaction include N-haloimides such as N-bromosuccinimide, N-chlorosuccinimide, N-bromoacetamide, N-bromophthalimide, isocyanuric bromide, isocyanuric chloride, N-bromocaprolactam and the like. Radical initiators may be added as a catalyst for the halogenation, including, for example, benzoyl peroxide, 2,2'-azobis(isobutyronitrile) and the like. The halogenation reaction may be facilitated by irradiation of actinic light such as visible light or UV light.

Using these agents and/or conditions, the compound to be halogenated is halogenated at the allyl position thereof in a solvent such as carbon tetrachloride, chloroform, ether, methanol, ethanol, acetone, water or the like. The subsequent dehydrohalogenation reaction may take place under the preceding halogenation reaction conditions without addition of any dehydrohalogenating agent. Of course, dehydrohalogenation agents may be added for the reaction. Examples of such dehydrohalogenating agents include organic bases such as pyridine, quinoline, collidine, triethylamine, tri-n-butylamine, dimethylaniline, 1,5-diazabicyclo[4.3.0]nonene-5, 1, 8-diazabicyclo[5.4.0]undecene-7, 1, 4-diazabicyclo[2.2.2]octane and the like, organic or inorganic bases such as potassium acetate, potassium carbonate, sodium carbonate, lithium carbonate and the like, phosphites such as trimethyl phosphite, triethyl phosphite and the like.

The oxidized or dehydrogenated compound is then subjected to desilylation reaction with an electrophilic reagent to obtain a halosilacyclohexane compound, followed by reduction reaction according to the following reaction sequence (17)

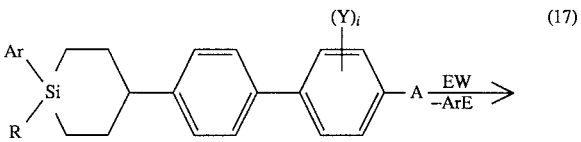

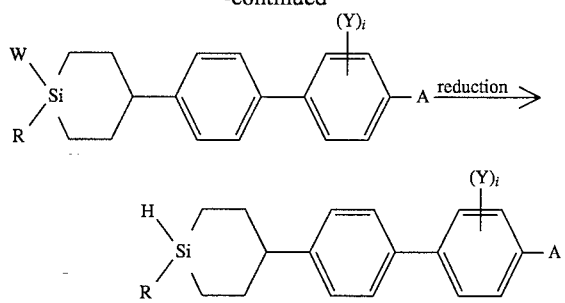

wherein EW represents an electrophilic reagent in which W represents a halogen, preferably Cl, I or Br.

The electrophilic reagents include, for example, halogens, hydrogen halides, metal halides, sulfonic derivatives, acid halides, alkyl halides and the like. Preferable examples include iodine, bromine, chlorine, iodine monochloride, hydrogen chloride, hydrogen bromide, hydrogen iodide, mercury (II) chloride, trimethylsilyl chlorosulfonate, acetyl chloride, acetyl bromide, benzoyl chloride, t-butyl chloride and the like. In order to increase the reaction velocity, addition of Lewis acids such as aluminium chloride, zinc chloride, titanium tetrachloride, boron trifluoride and the like or irradiation of visible light-or UV light is effective. The de-silylation reaction may be effected in a wide range of temperature. The reaction temperature is preferably in the range of from 0° to 80° C., more preferably from 10° to 40° C. The electrophilic reagent is preferably used in amounts of 1 to 5 equivalents, more preferably 1 to 2 equivalents per unit equivalent of the silacyclohexane compound.

The reagents used for the reduction of the resultant halosilacyclohexane compound include, for example, metal hydrides such as sodium hydride, calcium hydride, trialkylsilanes, boranes, dialkyl aluminium compounds and the like, complex hydrides such as lithium aluminohydride, sodium borohydride, lithium borohydride, potassium borohydride, tributylammonium borohydride and the like, and substituted hydrides thereof such as lithium trialkoxyaluminohydride, sodium di(methoxyethoxy)aluminohydride, lithium triethylborohydride, sodium cyanoborohydride and the like.

Although not limitative, the reduction of the halosilacyclohexane is carried out preferably at a temperature of from 0° to 150° C., more preferably from 20° to 100° C.

By the above process, there can be efficiently prepared the silacyclohexane-based liquid crystal compounds of the general formulas (I), (II) and (III).

The invention is more particularly described by way of examples.

EXAMPLE 1

Preparation of trans, trans-4-(4-n-pentyl-4-silacyclohexyl)-4'-(4-n-propylcyclohexyl)biphenyl 34.1 g of 4-(4-n-pentyl-4-phenyl-4-silacyclohexyl)-3-cyclohexenone was dropped in 250 ml of a tetrahydrofuran solution of 0.5 moles of trans-(4-n-propylcyclohexyl)phenylmagnesium chloride, followed by agitation at room temperature for 5 hours. The resultant mixture was charged into diluted hydrochloric acid and extracted with ether. The resultant ether solution was washed with brine, dried and concentrated, followed by addition, to the resultant residue, of 300 ml of benzene and 800 mg of p-toluenesulfonic acid monohydrate and removal of generated water under reflux. When the generation of water stopped, the benzene solution was washed with brine, dried and concentrated, followed by purification through column chromatography to obtain 36.8 g of 1-(4-n-pentyl-4-phenyl-4-silacylohexyl)-4-(trans-4-n-propylcyclohexyl)phenyl-1,3-cyclohexadiene at a yield of 70%. The results of $^1$H-NMR analysis of the compound are shown below. $^1$H-NMR (CDCl$_3$) δ:0.50–2.75(41H, m), 5.62–5.90(1H, m), 6.18–6.36(1H, m), 7.05–7.70(9H, m) ppm 5.00 g of the above compound was dissolved in 100 ml of benzene, to which 22.0 g of p-chloranil was added, followed by agitation for 3 hours under reflux. The mixture was diluted with methylene chloride and the resulting crystals were separated by filtration. The filtrate was concentrated and the resultant residue was purified through column chromatography to obtain 4.82 g (yield: 97%) of 4-(4-n-pentyl-4-phenyl-4-silacyclohexyl)-4'-(trans-4-n-propylcyclohexyl)biphenyl. The results of $^1$H-NMR analysis of the biphenyl compound are shown below. $^1$H-NMR (CDCl$_3$) δ:0.50–2.75 (37H, m), 7.05–7.70(13H, m) ppm 3.00 g of the compound was dissolved in 50 ml of carbon tetrachloride, followed by addition of 1.20 g of bromine monochloride and agitation at room temperature for 3 hours. The reaction mixture was concentrated and the resulting residue was dissolved in 20 ml of tetrahydrofuran, followed by dropping in a mixture of 250 mg of lithium aluminohydride and 10 ml of tetrahydrofuran. After agitation at room temperature for 20 hours, the mixture was charged into diluted hydrochloric acid and extracted with ethyl acetate. The resultant ethyl acetate solution was washed with brine, dried and concentrated, followed by column chromatography to obtain 1.33 g (yield: 52%) of the intended compound. The results of IR and NMR analyses are shown below.

IR (KBr disc) $v_{max}$: 2956, 2918, 2848, 2102, 1903, 1497, 1446, 985, 812 cm$^{-1}$ $^{13}$C-NMR (CDCl$_3$) δ: 10.59(s), 12.09(s), 13.99(s), 14.41(s), 20.03(s), 22.35(s), 24.06(s), 33.24(s), 33.58(s), 34.33(s), 35.37(s), 37.03(s), 39.73(s), 44.25(s), 47.27(s), 126.85(s), 127.00(s), 127.14(s), 138.65(s), 146.64(s), 147.44(s) ppm

EXAMPLE 2

Preparation of trans, trans-4-(4-n-propyl-4-silacyclohexyl)-4'-(4-n-propylcyclohexyl)biphenyl The general procedure of Example 1 was repeated using 32.7 g of 4-(4-n-propyl-4-phenyl-4-silacyclohexyl)-3-cyclohexenone, thereby obtaining the captioned compound. The results of IR, NMR and GC-MS analyses are shown below.

IR (KBr disc) $v_{max}$: 2954, 2918, 2848, 2104, 1901, 1497, 1444, 984, 810 cm$^{-1}$ $^{13}$C-NMR (CDCl$_3$) δ: 10.63(s), 14.43(s), 14.71(s), 17.82(s), 17.92(s), 20.05(s), 33.27(s), 33.60(s), 34.35(s), 37.05(s), 39.75(s), 44.26(s), 47.28(s), 126.83(s), 127.00(s), 127.14(s), 138.65(s), 146.62(s), 147.42(s)ppm GC-MS (70 eV) (m/z)$^+$: 69, 97, 193, 219, 320, 375, 418 (M$^+$)

EXAMPLE 3

Preparation of trans, trans-4-(n-propyl-4-silacyclohexyl)-4'-(4-n-pentylcyclohexyl)biphenyl The general procedure of Example 1 was repeated using 32.7 g of 4-(4-n-propyl-4-phenyl-4-silacyclohexyl)-3-cyclohexenone and 250 ml of a tetrahydrofuran solution of 0.5 moles of trans-(4-n-pentylcyclohexyl)phenylmagnesium bromide, thereby obtaining the captioned compound. The results of IR and NMR analyses are shown below.

IR (KBr disc) $v_{max}$: 2956, 2920, 2850, 2102, 1903, 1497, 1446, 985, 812 cm$^1$ $^{13}$C-NMR (CDCl$_3$)δ: 5:10.62(s), 14.12(s), 14.70(s), 17.81(s), 17.91(s), 22.73(s), 26.66(s), 32.23(s), 33.26(s), 33.63(s), 34.36(s), 37.34(s), 37.41(s), 44.27(s), 47.28(s), 126.88(s), 127.02(s), 127.15(s), 138.68(s), 146.67(s), 147.47(s) ppm

EXAMPLE 4

Preparation of trans, trans-4-(n-pentyl-4-silacyclohexyl)-4'-(4-n-pentylcyclohexyl)biphenyl The general procedure of Example 1 was repeated using 250 ml of a tetrahydrofuran solution of 0.5 moles of trans-4-(trans-4-n-pentylcyclohexyl)phenylmagnesium bromide, thereby obtaining the captioned compound. The results of IR and NMR analyses are shown below.

IR (KBr disc) $v_{max}$: 2956, 2920, 2850, 2104, 1498, 1456, 985, 887, 812 cm$^{-1}$ $^{13}$C-NMR (CDCl$_3$) δ: 10.60(s), 12.11, 14.00(s), 14.12(s), 22.36(s), 22.72(s), 24.07(s), 26.66(s), 32.22(s), 33.26(s), 33.63(s), 34.35(s), 35.37(s), 37.33(s), 37.40(s), 44.27(s), 47.28(S), 126.85(s), 126.88(s), 127.02(s), 127.15(s), 138.68(s), 146.68(s), 147.48(s) ppm

EXAMPLE 5

Preparation of trans, trans-4-(n-propyl-4-silacyclohexyl)-2'-fluoro-4'-(4-n-propylcyclohexyl)biphenyl The general procedure of Example 1 was repeated using 32.7 g of 4-(4-n-propyl-4-phenyl-4-silacyclohexyl)-3-cyclohexenone and 250 ml of a tetrahydrofuran solution of 0.5 moles of 2-fluoro-4-(trans-4-n-propylcyclohexyl)phenylmagnesium bromide, thereby obtaining the captioned compound. The results of IR and NMR analyses are shown below.

IR (KBr disc) $v_{max}$: 2954, 2922, 2850, 2098, 1493, 1404, 984, 887, 812 cm$^{-1}$ $^{13}$C-NMR (CDCl$_3$) δ: 10.62(s), 14.40(s), 14.70(s), 17.81(s), 17.91(s), 20.02 (s), 33.22(s), 33.44(s), 34.17(s), 36.98(s), 39.67(s), 44.09(s), 47.35(s), 114.23 (d), 122.74(d), 126.19(d), 126.73(s), 128.81(d), 130.27(d), 133.36(s), 147.85 (s), 149.30(d), 159.74(d) ppm

EXAMPLE 6

Preparation of trans, trans-4-(n-propyl-4-silacyclohexyl)-2'-fluoro-4'-(4-n-pentylcyclohexyl)biphenyl The general procedure of Example 1 was repeated using 32.7 g of 4-(4-n-propyl-4-phenyl-4-silacyclohexyl)-3-cyclohexenone and 250 ml of a tetrahydrofuran solution of 0.5 moles of 2-fluoro-(trans-4-n-pentylcyclohexyl)phenylmagnesium bromide, thereby obtaining the captioned compound. The results of IR and NMR analyses are shown below.

IR (KBr disc) $v_{max}$: 2952, 2922, 2850, 2100, 1493, 1446, 1404, 984, 887, 812 cm$^{-1}$ $^{13}$C-NMR (CDCl$_3$) δ: 10.62(s), 14.12(s), 14.70(s), 17.81(s), 17.92(s), 22.72 (s), 26.65(s), 32.21(s), 33.22(s), 33.47(s), 34.17(s), 37.27(s), 37.34(s), 44.10 (s), 47.35(s), 114.23(d), 122.74(d), 126.19(d), 126.73(s), 128.80(d), 130.27 (d), 133.36(s), 147.84(s), 149.29(d), 159.74(d) ppm

EXAMPLE 7

Preparation of trans, trans-4-(n-pentyl-4-silacyclohexyl)-2'-fluoro-4'-(4-n-propylcyclohexyl)biphenyl The general procedure of Example 1 was repeated using 250 ml of a tetrahydrofuran solution of 0.5 moles of 2-fluoro-4-(trans-4-n-propylcyclohexyl)phenylmagnesium bromide, thereby obtaining the captioned compound. The results of IR and NMR analyses are shown below.

IR (KBr disc) $v_{max}$: 2952, 2918, 2850, 2100, 1490, 1404, 985, 887, 879, 814 cm$^{-1}$ $^{13}$C-NMR (CDCl$_3$) δ:10.59(s), 12.11(s), 14.01(s), 14.40(s), 20.03(s), 22.37 (s), 22.37(s), 24.07(s), 33.22(s), 33.43(s), 34.17(s), 35.38(s), 36.97(s), 39.67 (s), 44.09(s), 47.36(s), 114.22(d), 122.77(d), 126.19(d), 126.73(s), 128.80(d), 130.27(d), 133.36(s), 147.84(s), 149.28(d), 159.74(d) ppm

EXAMPLE 8

Preparation of trans, trans-4-(n-pentyl-4-silacyclohexyl)-2'-fluoro-4'-(4-n-propylcyclohexyl)biphenyl The general procedure of Example 1 was repeated using 250 ml of a tetrahydrofuran solution of 0.5 moles of 2-fluoro-4-(trans-4-n-pentylcyclohexyl)phenylmagnesium chloride, thereby obtaining the captioned compound. The results of IR and NMR analyses are shown below.

IR (KBr disc) $\nu_{max}$: 2952, 2922, 2850, 2102, 1493, 1446, 1404, 985, 814 cm$^{-1}$ $^{13}$C-NMR (CDCl$_3$) δ:10.59(s), 12.10(s), 14.00(s), 14.11(s), 22.36(s), 22.71 (s), 24.07(s), 26.64(s), 32.21(s), 33.21(s), 33.47(s), 34.17(s), 35.37(s), 37.26 (s), 37.33(s), 44.10(s), 47.35(s), 114.22(d), 122.78(d), 126.07(d), 126.73(s), 128.78(d), 130.30(d), 133.35(s), 147.85(s), 149.34(d), 159.73(d) ppm

EXAMPLE 9

Preparation of trans-4-(4-n-pentyl-4-silacyclohexyl)-4'-fluorobiphenyl

In the same manner as in Example 1, 50.0 g of 4-(4-n-pentyl-4-phenyl-4-silacyclohexyl)-2-cyclohexenone was subjected to coupling reaction with 4-fluorophenyllithium, followed by dehydration reaction in the presence of an acid catalyst to obtain 45.5 g of 1-(4-n-pentyl-4-phenyl-4-silacyclohexyl)-4-(4-fluorophenyl)-1,3-cyclohexadiene (yield: 74%). The results of IR analysis of the compound are shown below.

IR (liquid film) $\nu_{max}$: 2920, 2860, 1595, 1505, 1230, 1110, 980, 820 cm$^{-1}$ 200 ml of carbon tetrachloride, 13.0 g of N-bromosuccinimide and 50 mg of benzoyl peroxide was added to 35.0 g of the thus obtained compound, followed by agitation under reflux for 3 hour. The reaction mixture was washed with a sodium hydrogencarbonate aqueous solution and the carbon tetrachloride solution was dried and concentrated. The resultant residue was purified to obtain 28.9 g of 4-(4-n-pentyl-4-phenyl-4-silacyclohexyl)-4'-fluorobiphenyl (yield: 83%). The results of GC-MS analysis of the compound are shown below.

GC-MS (70 eV) (m/z)$^+$: 158, 240, 290, 338, 360, 416 (M$^+$)

25.0 g of the thus obtained compound was subjected to de-silylation reaction with iodine monochloride in the same manner as in Example 1 and then to reduction with lithium aluminohydride to obtain 13.1 g of the captioned compound (yield: 64%). The results of IR and NMR analyses are shown below.

IR (KBr disc) $\nu_{max}$: 2916, 2852, 2096, 1495, 1238, 982, 883, 835, 810 cm$^{-1}$ $^{13}$C-NMR (CDCl$_3$) δ:10.58(s), 12.08(s), 14.00(s), 22.36(s), 24.06(s), 33.25 (s), 35.37(s), 47.27(s), 115.49(d), 126.89(s), 127.16(s), 128.46(d), 137.72(s), 147.87(s), 162.27(d)ppm

EXAMPLE 10

Preparation of trans-4-(4-n-pentyl-4-silacyclohexyl)-3'-fluoro-4'-chlorobiphenyl The general procedure of Example 1 was repeated using 3-fluoro-4-chlorophenyllithium, thereby obtaining the captioned compound. The results of IR analysis are shown below.

IR (KBr disc) $\nu_{max}$: 2953, 2916, 2870, 2108, 1479, 1396, 1200, 985, 879, 812 cm$^{-1}$

EXAMPLE 11

Preparation of trans-4-(4-ethyl-4-silacyclohexyl)-4'-fluorobiphenyl

The general procedure of Example 1 was repeated using 30.0 g of 4-(4-ethyl-4-phenyl-4-silacyclohexyl)-2-cyclohexenone, thereby obtaining the captioned compound. The results of IR and NMR analyses are shown below.

IR (KBr disc) $\nu_{max}$: 2956, 2916, 2873, 2096, 1495, 1238, 966, 887, 881, 814 cm$^{-1}$ $^{13}$C-NMR (CDCl$_3$) δ:4.03(s), 7.90(s), 9.98(s), 33.15(s), 47.25(s), 115.48(d), 126.87(s), 127.14(s), 128.43(d), 137.22(d), 137.68(s), 147.81(s), 162.26(d) ppm

EXAMPLE 12

Preparation of trans-4-(4-n-propyl-4-silacyclohexyl)-4'-fluorobiphenyl

In the same manner as in Example 1, 35.0 g of 4-(4-n-propyl-4-phenyl-4-silacyclohexyl)cyclohexanone were subjected to coupling reaction with 4-fluorophenylmagnesium chloride, followed by dehydration reaction in the presence of an acid catalyst to obtain 35.9 g of 4-(4-n-propyl-4-phenyl-4-silacyclohexyl)-1-(4-fluorophenyl)-1-cyclohexene (yield: 82%). The results of $^1$H-NMR analysis are shown below. $^1$H-NMR (CDCl$_3$) δ:0.50–2.55 (23H, m), 5.90–6.14 (1H, m), 6.80–7.65 (9H, ppm 30.0 g of the thus obtained compound was dissolved in 600 ml of 1,4-dioxane, to which 35.0 g of 2,3-dichloro-t,6-dicyano-1,4-benzoquinone (DDQ) was added, followed by agitation under reflux for 8 hours and also by after-treatment and purification in the same manner as in Example 1 to obtain 18.5 g of 4-(4-n-propyl-4-phenyl-4-silacyclohexyl)-4'-fluorobiphenyl (yield: 62%). The results of NMR analysis are shown below. $^1$H-NMR (CDCl$_3$) δ:0.50–2.60 (16H, m), 6.88–7.65 (13H, m) ppm 12.8 g of the thus obtained compound was subjected to de-silylation with iodine monochloride in the same manner as in Example 1 and then to reduction with lithium aluminohydride to obtain 6.62 g of the captioned compound (yield: 64%). The results of IR and NMR analyses are shown below.

IR (KBr disc) $\nu_{max}$: 2954, 2918, 2856, 2087, 1497, 1238, 1163, 987, 889, 881, 816 cm$^{-1}$ $^{13}$C-NMR (CDCl$_3$) δ:10.60(s), 14.67(s), 17.79(s), 17.90(s), 33.25(s), 47.26 (s), 115.49(d), 126.88(s), 127.16(s), 128.46(d), 137.25(d), 137.72(s), 147.86 (s), 162.28(d) ppm

EXAMPLE 13

Preparation of trans-4-(4-n-pentyl-4-silacyclohexyl)-4'-trifluoromethoxybiphenyl The general procedure of Example 12 was repeated using 34.3 g of 4-(4-n-pentyl-4-phenyl-4-silacyclohexyl)cyclohexanone and trifluoromethoxyphenylmagnesium bromide, thereby obtaining the captioned compound. The results of IR and NMR analyses are shown below.

IR (KBr disc) $\nu_{max}$: 2916, 2852, 2092, 1497, 1263, 1211, 1163, 987, 890, 881, 808 cm$^{-1}$ $^{13}$C-NMR (CDCl$_3$) δ:10.57(s), 12.08(s), 13.99(s), 22.37(s), 24.06(s), 33.24 (s), 35.37(s), 47.30(s), 120.54 (q), 121.13(s), 126.99(s), 127.24(s), 128.23(s), 137.30(s), 139.91(s), 148.32(s), 148.42(d) ppm

EXAMPLE 14

Preparation of trans-4-(4-(3-methylbutyl)-4-silacyclohexyl)-3', 4'-difluorobiphenyl The general procedure of Example 12 was repeated using 34.3 g of 4-(4-(3-methylbutyl)-4-phenyl-4-silacyclohexyl)cyclohexanone and 3,4-difluorophenylmagnesium bromide, thereby obtaining the captioned compound.

EXAMPLE 15

Preparation of trans-4-(4-(3-methoxypropyl)-4-silacyclohexyl)-3', 4'-difluorobiphenyl The general procedure of Example 12 was repeated using 34.5 g of 4-(4-(3-methoxypropyl)-4-phenyl-4-silacyclohexyl)cyclohexanone and 3,4-difluorophenylmagnesium bromide, thereby obtaining the captioned compound.

EXAMPLE 16

Preparation of trans-4-(4-(3-pentenyl)-4-silacyclohexyl)-3', 4'-difluorobiphenyl The general procedure of Example 12 was repeated using 34.1 g of 4-(4-(4-pentenyl)-4-phenyl-4-silacyclohexyl)cyclohexanone and 3,4-difluorophenylmagnesium bromide, thereby obtaining the captioned compound.

EXAMPLE 17

Preparation of trans-4-(4-ethyl-4-silacyclohexyl)-3', 4'-difluorobiphenyl

The general procedure of Example 12 was repeated using 30.2 g of 4-(4-ethyl-4-phenyl-4-silacyclohexyl)cyclohexanone and 3,4-difluorophenylmagnesium bromide, thereby obtaining the captioned compound.

EXAMPLE 18

Preparation of trans-4-(4-n-propyl-4-silacyclohexyl)-3',4'-difluorobiphenyl

The general procedure of Example 12 was repeated using 3,4-difluorophenylmagnesium bromide, thereby obtaining the captioned compound. The results of IR and NMR analyses are shown below.

IR (liquid film) $v_{max}$: 2956, 2918, 2873, 2100, 1529, 1504, 1403, 1119, 985, 889, 877, 811 cm$^{-1}$ $^{13}$C-NMR (CDCl$_3$) δ:10.59(s), 14.66(s), 17.79(s), 17.90(s), 33.22(s), 47.27 (s), 115.75(d), 117.38(d), 122.74 (dd), 126.83(s), 127.29(s), 136.61(s), 138.28 (dd), 148.27 (dd), 148.49(s), 15 1.92 (dd) ppm

EXAMPLE 19

Preparation of trans-4-(4-n-pentyl-4-silacyclohexyl)-3',4'-difluorobiphenyl

The general procedure of Example 12 was repeated using 34.3 g of 4-(4-n-pentyl-4-phenyl-4-silacyclohexyl)cyclohexanone and 3,4-difluorophenylmagnesium bromide, thereby obtaining the captioned compound. The results of IR and NMR analyses are shown below.

IR (KBr, disc) $v_{max}$: 2958, 2916, 2850, 2108, 1605, 1527, 1506, 1269, 985, 879, 831, 812 cm$^{-1}$ $^{13}$C-NMR (CDCl$_3$) δ:10.57(s), 12.06(s), 13.99(s), 22.36(s), 24.05(s), 33.22 (s), 35.37(s), 47.28(s), 115.75(d), 117.38(d), 122.74 (dd), 126.83(s), 127.29(s), 136.63(s), 138.28 (dd), 148.27 (dd), 148.49(s), 15 1.92 (dd) ppm

EXAMPLE 20

Preparation of trans-4-(4-n-pentyl-4-silacyclohexyl)-4"-fluoroterphenyl

The general procedure of Example 12 was repeated using 34.3 g of 4-( 4-n-pentyl-4-phenyl-4-silacyclohexyl)cyclohexanone and 4-(4-fluorophenyl)phenylmagnesium bromide, thereby obtaining the captioned compound. The results of IR and NMR analyses are shown below.

IR (KBr, disc) $v_{max}$: 2954, 2916, 2852, 2098, 1493, 1240, 1160, 887, 883, 835, 811 cm$^{-1}$ $^{13}$C-NMR (CDCl$_3$) δ: 10.59(s), 12.09(s), 14.00(s), 22.37(s), 24.07(s), 33.25 (s), 35.37(s), 47.31(s), 115.65(d), 126.91(s), 127.19(s), 127.27(s), 127.36(s), 128.52(d), 136.88(d), 138.04(s), 138.78(s), 140.07(s), 148.05(s), 162.46(d) ppm

EXAMPLE 21

Preparation of trans-4-(4-n-pentyl-4-silacyclohexyl)-3", 4"-difluoroterphenyl

The general procedure of Example 12 was repeated using 34.3 g of 4-(4-n-pentyl-4-phenyl-4-silacyclohexyl)cyclohexanone and 4-(3,4-difluorophenyl)phenylmagnesium bromide, thereby obtaining the captioned compound. The results of IR and NMR analyses are shown below.

IR (KBr, disc) $v_{max}$: 2956, 2916, 2854, 2110, 1495, 985, 887, 881, 810 cm$^{-1}$ $^{13}$C-NMR (CDCl$_3$) δ: 10.58(s), 12.08(s), 14.00(s), 22.37(s), 24.06(s), 33.24 (s), 35.37(s), 47.31(s), 115.80(d), 117.52(d), 122.81 (dd), 126.19(s), 127.22(s), 127.45(s), 137.88(s), 137.89 (dd), 140.63(s), 148.21(s), 148.39 (dd), 152.04 (dd) ppm

What is claimed is:

1. A process for preparing a silacyclohexane-based liquid crystal compound of the following formula (I)

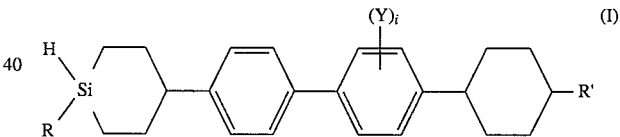

wherein R represents a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms or an alkoxyalkyl group having from 2 to 7 carbon atoms, Y represents a halogen or CH$_3$, and i is a value of 0, 1, 2 or 3, and R' represents a linear alkyl group having from 1 to 10 carbon atoms, a mono or difluoroalkyl group having from 1 to 10 carbon atoms, a branched alkyl group having from 3 to 8 carbon atoms or an alkoxyalkyl group having from 2 to 7 carbon atoms, the process comprising the steps of:

(1) subjecting a ketone compound of the following formula

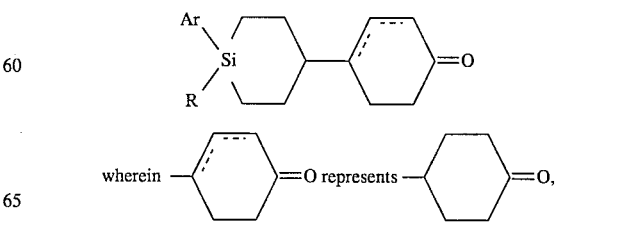

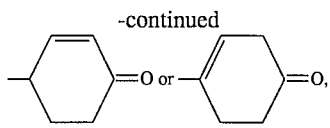

Ar represents a phenyl group or a tolyl group, R has the same meaning as defined above, to reaction with an organometal reagent of the following formula

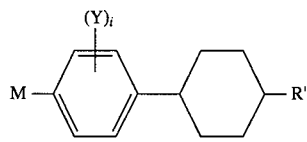

wherein M represents Li, MgU, ZnU or $TiU_k(OW)_{3-k}$ in which U represents a halogen, W represents an alkyl group, and k is zero or an integer of 1 to 3, Y, i and R' have, respectively, the same meanings as defined in the formula (I) to obtain a compound of the following formula

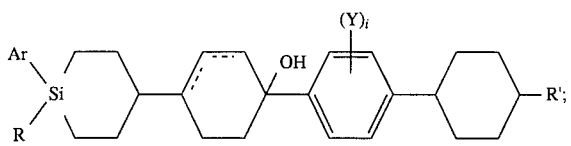

(2) subjecting the compound of the above general formula to dehydration and then to oxidation to obtain a compound of the following formula

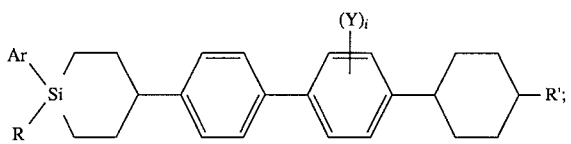

and (3) subjecting the thus obtained compound of the above formula to de-silylation and then to reduction to obtain the silacyclohexane-based compound of the general formula (I) defined hereinabove.

2. A process according to claim 1, wherein Y is F or Cl.

3. A process according to claim 1, wherein when said organometal reagent consists of an organolithium metal, the reaction of the step (1) is effected at a temperature ranging from −70° C. to 0° C. and when said organometal reagent consists of a member selected from the group consisting of Grignard reagents, organozinc reagents and organotitanium reagents, the reaction is effected at a temperature ranging from room temperature to 150° C.

4. A process according to claim 1, wherein the dehydration reaction in the step (2) is effected in a hydrocarbon solvent under azeotropic conditions whereby generated water is quickly azeotropically removed from a reaction system.

5. A process according to claim 1, wherein the oxidation in step (2) is effected by catalytic dehydrogenation reaction in the presence of a metal catalyst.

6. A process according to claim 1, wherein the oxidation in step (2) is effected by dehydrogenation reaction with a quinone.

7. A process according to claim 1, wherein the oxidation in step (2) is effected by halogenation and dehydrohalogenation reaction.

8. A process for preparing another type of silacyclohexaneo-based liquid crystal compound of the following formula (II)

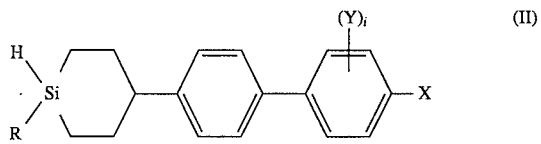

wherein R represents a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms or an alkoxyalkyl group having from 2 to 7 carbon atoms, Y represents a halogen or $CH_3$, and i is a value of 0, 1, 2 or 3, and X represents R or OR, wherein R has the same meaning as defined above, CN, F, Cl, Br, $CF_3$, $OCF_3$, $OCHF_2$, $OCHFCl$, $OCF_2Cl$, $CF_2Cl$, $—(O)_m—C\ Y_1=CX_1X_2$ wherein m is a value of 0 or 1, $Y_1$ and $X_1$, respectively, represent H, F or Cl, and $X_2$ represents F or Cl, or $—O—(CH_2)_r(CF_2)_sX_3$ wherein r and s are, respectively, a value of 0, 1 or 2 provided that r+s=2, 3 or 4, and $X_3$ represents H, F or Cl, the process comprising the steps of:

(1) subjecting a ketone compound of the following formula

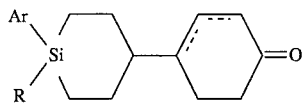

wherein 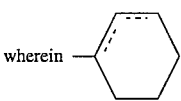 represents 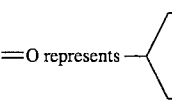

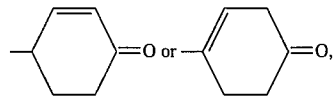

Ar represents a phenyl group or a tolyl group, R has the same meaning as defined above, to reaction with an organometal reagent of the following formula

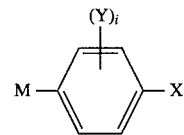

wherein M represents Li, MgU, ZnU or $TiU_k(OW)_{3-k}$ in which U represents a halogen, W represents an alkyl group, and k is zero or an integer of 1 to 3, Y, i and X have, respectively, the same meanings as defined above to obtain a compound of the following formula

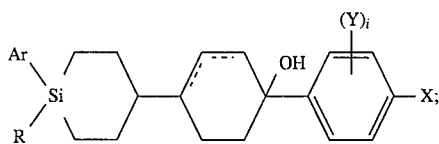

(2) subjecting the thus obtained compound of the above formula to dehydration and then to oxidation to obtain a compound of the following formula

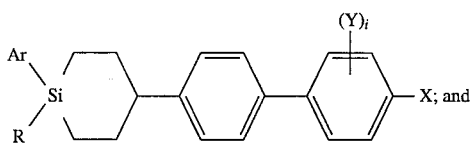

(3) subjecting the thus obtained compound of the above formula to de-silylation and then to reduction to obtain the silacyclohexane-based compound of the formula (II) defined above.

9. A process according to claim 8, wherein Y is F or Cl.

10. A process according to claim 8, wherein when said organometal reagent consists of a organolithium metal, the reaction of the step (1) is effected at a temperature ranging from −70° C. to 0° C. and when said organometal reagent consists of a member selected from the group consisting of Grignard reagents, organozinc reagents and organotitanium reagents, the reaction is effected at a temperature ranging from room temperature to 150° C.

11. A process according to claim 8, wherein the dehydration reaction in the step (2) is effected in a hydrocarbon solvent under azeotropic conditions whereby generated water is quickly azeotropically removed from a reaction system.

12. A process according to claim 8, wherein the oxidation in step (2) is effected by catalytic dehydrogenation reaction in the presence of a metal catalyst.

13. A process according to claim 8, wherein the oxidation in step (2) is effected by dehydrogenation reaction with a quinone.

14. A process according to claim 8, wherein the oxidation in step (2) is effected by halogenation and dehydrohalogenation reaction.

15. A process for preparing a silacyclohexane-based liquid crystal compound of the following formula (III)

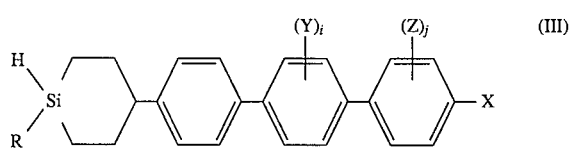

wherein R represents a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms or an alkoxyalkyl group having from 2 to 7 carbon atoms, Y represents a halogen or $CH_3$, and i is a value of 0, 1, 2 or 3, and X represents R or OR, wherein R has the same meaning as defined above, CN, F, Cl, Br, $CF_3$, $OCF_3$, $OCHF_2$, $OCHFCl$, $OCF_2Cl$, $CF_2Cl$, $—(O)_m—C\ Y_1=CX_1X_2$ wherein m is a value of 0 or 1, $Y_1$ and $X_1$, respectively, represent H, F or Cl, and $X_2$ represents F or Cl, or $—O—(CH_2)_r(CF_2)_sX_3$ wherein r and s are, respectively, a value of 0, 1 or 2 provided that r+s=2, 3 or 4, and $X_3$ represents H, F or Cl, Z represents a halogen or $CH_3$, and j is a value of 0, 1, 2 or 3, the process comprising the steps of:

(1) subjecting a ketone compound of the following formula

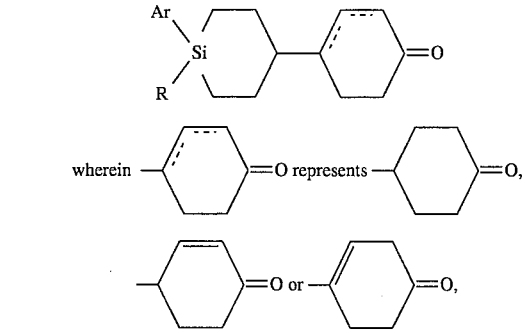

wherein 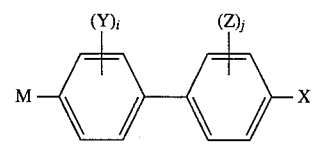 represents

Ar represents a phenyl group or a tolyl group, R has the same meaning as defined above, to reaction with an organometal reagent of the following formula

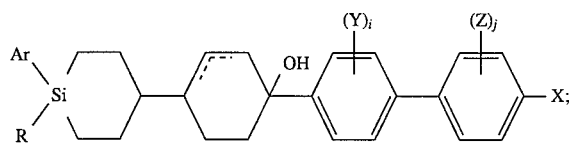

wherein M represents Li, MgU, ZnU or $TiU_k(OW)_{3-k}$ in which U represents a halogen, W represents an alkyl group atoms, and k is zero or an integer of 1 to 3, Y, Z, i, j and X have, respectively, the same meanings as defined above to obtain a compound of the following formula

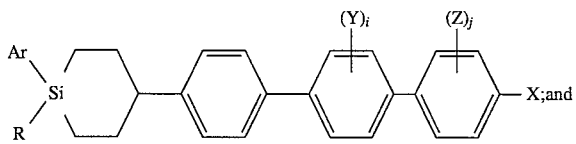

(2) subjecting the compound of the formula (9) to dehydration and then to oxidation, to obtain a compound of the following formula (3) subjecting the thus obtained compound of the above formula to de-silylation and then to reduction to obtain the silacyclohexane-based compound of the formula (III) defined above.

16. A process according to claim 15, wherein Y is F or Cl.

17. A process according to claim 15, wherein when said organometal reagent consists of a organolithium metal, the reaction of the step (1) is effected at a temperature ranging from −70° C. to 0° C. and when said organometal reagent consists of a member selected from the group consisting of Grignard reagents, organozinc reagents and organotitanium reagents, the reaction is effected at a temperature ranging from room temperature to 150° C.

18. A process according to claim 15, wherein the dehydration reaction in the step (2) is effected in a hydrocarbon solvent under azeotropic conditions whereby generated water is quickly azeotropically removed from a reaction system.

19. A process according to claim 15, wherein the oxidation in step (2) is effected by catalytic dehydrogenation reaction in the presence of a metal catalyst.

20. A process according to claim 15, wherein the oxidation in step (2) is effected by dehydrogenation reaction with a quinone.

21. A process according to claim 15, wherein the oxidation in step (2) is effected by halogenation and dehydrohalogenation reaction.

* * * * *